(12) United States Patent
Waizenegger (10) Patent No.: US 11,191,577 B2
(45) Date of Patent: Dec. 7, 2021

(54) ORTHOGNATHIC SAWING AND POSITIONING IMPLANT

(71) Applicant: Firma Karl Leibinger Medizintechnick GmbH & Co. KG, Muhlheim (DE)

(72) Inventor: Axel Waizenegger, Muhlheim (DE)

(73) Assignee: KARL LEIBINGER MEDIZINTECHNIK GMBH & CO. KG.

( * ) Notice: Subject to any disclaimer, the term of this patent is extended or adjusted under 35 U.S.C. 154(b) by 332 days.

(21) Appl. No.: 16/538,061

(22) Filed: Aug. 12, 2019

(65) Prior Publication Data

US 2019/0357952 A1    Nov. 28, 2019

Related U.S. Application Data

(62) Division of application No. 15/153,426, filed on May 12, 2016, now abandoned.

(30) Foreign Application Priority Data

May 12, 2015   (DE) .................................. 16483400

(51) Int. Cl.
| | |
|---|---|
| A61B 17/56 | (2006.01) |
| A61B 17/58 | (2006.01) |
| A61B 17/80 | (2006.01) |
| A61B 34/10 | (2016.01) |
| A61B 17/17 | (2006.01) |
| A61B 17/00 | (2006.01) |

(52) U.S. Cl.
CPC ........ *A61B 17/8071* (2013.01); *A61B 17/176* (2013.01); *A61B 17/1728* (2013.01); *A61B 34/10* (2016.02); *A61B 2017/00004* (2013.01); *A61B 2017/568* (2013.01); *A61B 2034/104* (2016.02); *A61B 2034/108* (2016.02)

(58) Field of Classification Search
CPC .............................. A61B 17/56; A61B 17/58
See application file for complete search history.

(56) References Cited

U.S. PATENT DOCUMENTS

2015/0272598 A1* 10/2015 Dubois .............. A61B 17/8071
                                                          606/280

FOREIGN PATENT DOCUMENTS

WO    WO-2014090964 A2 *  6/2014 ............. A61B 34/10

\* cited by examiner

*Primary Examiner* — Samuel S Hanna
(74) *Attorney, Agent, or Firm* — Thomas C. Saitta (57) ABSTRACT

An orthognathic bone joining or positioning implant method for performing an osteotomy and subsequent rejoining of one or more separated bone sections to the bone in a desired repositioning, wherein the implant is manufactured such that it provides a separating tool guidance contour for separating the bone sections after attaching a first attachment area to the bone, and provides a second or third attachment area for attaching the separated bone sections to the bone in the desire repositioning without detaching said first attachment area. The method utilizes tomographic imaging to produce a target 3D model of the bone showing the repositioned bone sections based on the original 3D model of the bone.

18 Claims, 6 Drawing Sheets

ORTHOGNATHIC SAWING AND POSITIONING IMPLANT

BACKGROUND OF THE INVENTION AND SUMMARY

The invention concerns an orthognathic bone joining implant (also referred to as a positioning implant) for an osteotomy application/joining of a first bone section with a second bone section or several bone sections of a mammal bone/bone of a mammal with a first attachment area displaying several holes for fastening elements, prepared for attachment to the first bone area, and a second attachment area linked to the first attachment area, with the second attachment area also displaying several holes for fastening elements, also prepared for attachment to the second bone section. Especially in the case of a bisected lower jaw, for instance with a crowding of the lower jaw, there are several bone sections to which the first bone section will be joined. A mammal bone/bone of a mammal is defined as an especially hard, skeleton growing supporting tissue of a vertebrate, that is to say, such a structure made of bone tissue. This includes in particular such bones as the fibula and tibia, but also cranial bones.

Bone joining implants in conformity with their kind are already known at the current technology status. In this context, WO 2014/090964 A2 for instance reveals a guide, together with a procedure for its configuration. The implant as well as the guide are intended for osteotomy applications at a patient's maxilla and may be designed as a kit. The three dimensional models of the pre and post-operative anatomy are used to define the attachment areas for the guide and the implant. Those attachment areas will then further be used to define the structure of the implant as well as the guide. The technology status is further known from EP 2 698 122 A1 and WO 2011/136898 A1.

Those designs known from the technology status, however, for the most part have the disadvantage that two separate elements must be used for separating the mammal bones that are to be corrected and then joined again, such as, for example a maxilla or mandible. Preferably, the cutting of the mammal bone is performed through a sawing procedure, with a template-like tool guidance, and the joining of the two formerly separated bone sections in the desired position is done with an implant. Thus, in the past, any osteotomy applications always required the manufacture of a user defined tool guidance as well as a user defined positioning implant. This resulted in a relatively extensive manufacture of the elements used for the osteotomy applications and therefore relatively high surgery cost.

Therefore, the task of this invention is to remedy these disadvantages known from the technology status and, in particular, to provide a bone joining implant that will further reduce the extent of an osteotomy treatment, while maintaining at the same time a patient specific/individualized adjustment of the bone joining implant.

The solution provided by the invention is the formation of a (first) separating tool guidance contour between the first and second attachment area, defining a (first) cutting line. A position between the first and the second attachment area means any (spatial) position, viewed in its spatial extension along the mammal bone, located between the first and second attachment areas. Thus, the separating tool guidance contour is located between a side of the first attachment area, facing the second attachment area, and a side of the second attachment area, facing the first attachment area.

This design permits the use of the bone joining implant not only as a positioning implant but also as a separating template for the previous separation of the two sections of the mammal bone. This allows for an especially cost efficient correction of the relevant malformation of the mammal bone. It should be pointed out that a further advantage of using the same implant for cutting and then joining is, in particular, the avoidance of any manufacturing tolerances between the tool guidance, previously manufactured separately, and the positioning implant. After joining, the two bone sections are then located in relation to each other with a notably higher precision, corresponding to the previously calculated target position, which will in turn foster the healing process of the mammal bone.

Any further design advantages are being claimed in the sub-claims and described in more detail below.

The bar design of the separating tool guidance contour provides an additional advantage. This creates a stabile support of the cutting tool, such as a saw/buzz saw, on the separating tool guidance contour, in order to cut the two bone sections along the separating line/osteotomy line.

A further advantage is provided by a design directly linking the separating tool guidance contour with a bridge between the first attachment area and/or the second attachment area. This creates an especially compact structure of the bone joining implant.

If the separating tool guidance contour is designed with an interior edge of a frame structure located between the first and the second attachment area, this serves the purpose of placing the separating tool guidance contour in a particularly dimensionally stable section of the bone joining implant whose structure cannot simply be altered by the cutting operation.

If the (first and second) attachment areas and the separating tool guidance contour are designed/linked integrally/in one part, the bone joining implant will be even more stable. This further enhances the formal stability between the attachment areas and the separating tool guidance contour.

A further advantage is provided by manufacturing the bone joining implant from a biocompatible and/or biodegradable substance/made entirely from that substance. This will allow for a particularly efficient use of the bone joining implant.

In this context, manufacture of the bone joining implant from a metal substance, preferably a titanium substance, will also afford a particular advantage. Preferably, the titanium substance will receive heat treatment. This will create a particularly dimensionally stable bone joining implant.

It is advisable to create an additional/second separating tool guidance contour between the second attachment area and an additional third attachment area, defining a (second) separating line, with the third attachment area again displaying several holes to receive the fastening elements and prepared for attachment to the first bone section. Thus, the link between the two bone sections will be even more stable, with both bone sections being linked to each other in a secured position. In this context, the second separating tool guidance contour will preferably be designed in the same way as the first separating tool guidance contour.

A further advantage would be to prepare the bone joining implant for joining the first bone section with the second bone section of a maxilla bone/maxilla or a mandible bone/mandible. Thus, the bone joining implant will be particularly efficient.

The invention further concerns a procedure for the individualized manufacture of the bone implant based on at least one of the previously described designs, comprising the following steps, preferably in a timely sequence:

a) Obtaining a first data set of a 3D model of the mammal bone to be treated, in its existing condition;

b) Creating a second data set of a 3D target model, defining at least one separating line on the 3D model of the existing condition and a relative shift of two imaginary bone sections to each other (namely, the first bone section in relation to the second bone section), and c) Manufacture of the bone joining implant based on the 3D target model/second data set, creating the first attachment area for attachment to the first (imaginary) bone section of the 3D target model, the second attachment area for attachment to the second (imaginary) bone section of the 3D target model and the separating tool guidance contour by recreating, at least in part, the cutting line.

This will allow for a particularly effective manufacture of the bone joining implant.

The invention further concerns a procedure for the treatment of a mammal bone, preferably human, using a bone joining implant in accordance with one of the previously described designs, comprising the following steps:

a) Attaching the bone joining implant to a first attachment area located on the first bone section of the mammal bone;

b) Cutting the mammal bone along the separation line, installing a separating tool on the separating tool guidance contour;

c) Aligning the second bone section, separated from the first bone section, in the desired target position, and d) Attaching the second attachment area to the second bone section.

This allows for a particularly effective treatment procedure.

BRIEF DESCRIPTION OF THE DRAWINGS

In the following, the invention is further described based on diagrams, showing in FIG. 1 an isometric representation of a bone joining implant, based on the invention, in accordance with a favorable design model, displaying particularly well a first and second attachment area as well as a (first) separating tool guidance contour formed along a bridge of the first attachment area.

DETAILED DESCRIPTION OF THE INVENTION

Those figures are solely schematic in nature and are exclusively designed for a better understanding of the invention. Identical elements are marked with the identical reference.

Figure 1:
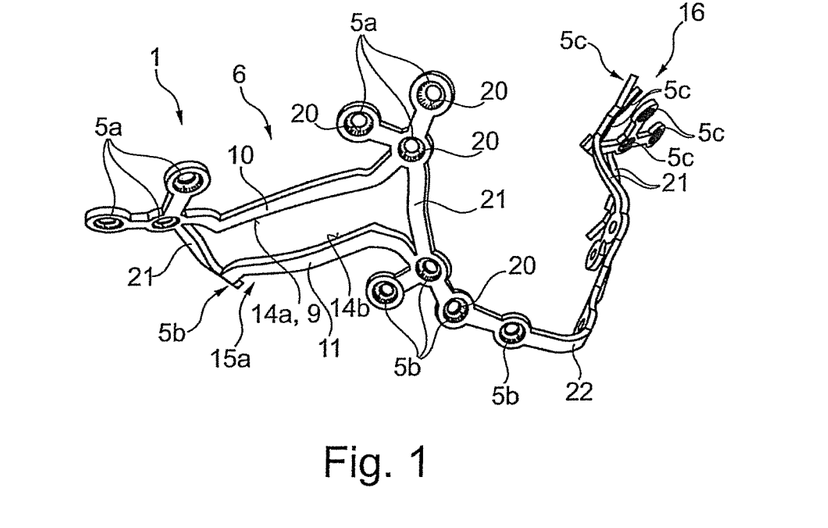

In FIG. 1, a bone joining implant 1 is displayed particularly well, based on the invention, in accordance with a preferred design example. That figure displays a first attachment area 6, showing several holes for receiving fastening elements 5a, prepared for attachment to a first bone section 2 of a mammal bone 4, as well as a second attachment area 7, linked to the first attachment area 6. The second attachment area 7 also displays several holes for receiving fastening elements, hereafter referred to as the second holes for receiving fastening elements 5b, thus preparing the second attachment area 7 for attachment of a second bone section 3 of the mammal bone 4.

Figure 2:
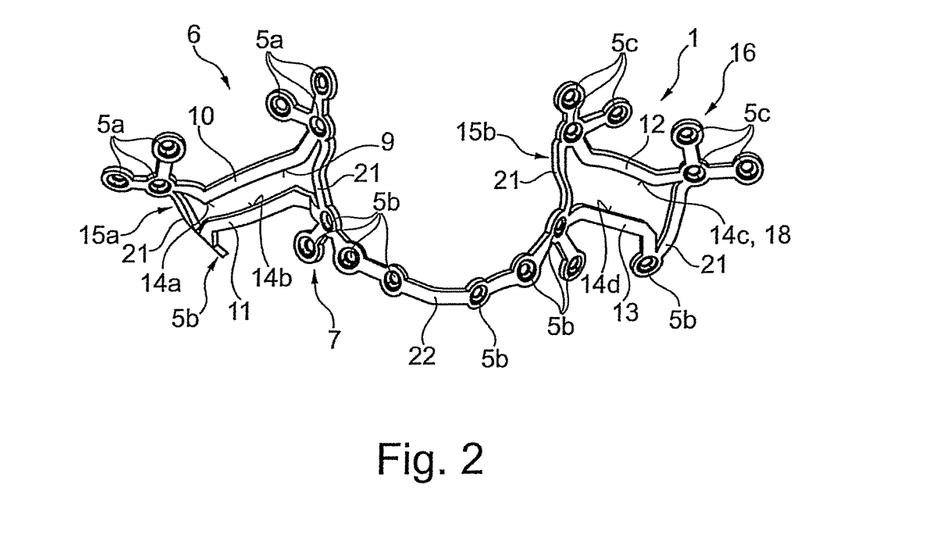
FIG. 2 a frontal view of the bone joining implant shown in FIG. 1, now showing in addition to the first and second attachment areas an additional, third attachment area, also linked to the second attachment area, with the third attachment area also displaying a bridge forming a (second) separating tool guidance contour.

Clearly visible in FIG. 2 is the second attachment area 7, essentially formed by a principal bridge 22, also linked to a third attachment area 16. The second holes for fastening elements 5b are placed side by side in a chainlike manner on the principal bridge 22. As described below, the principal bridge 22 again forms a second and fourth bridge 11, 13. The third attachment area 16 is essentially formed similarly to the first attachment area 6, also displaying several holes for fastening elements that are hereafter referred to as the third set of holes for receiving fastening elements 5c. As described below in more detail, this third set of holes for receiving fastening elements 5c is designed for the attachment to the first bone section 2. The first attachment area 6 as well as the third attachment area 16 each display two groups of first and third holes for receiving fastening elements 5a, 5c, respectively, placed in a triangular formation relative to each other.

The first set of holes for receiving fastening elements 5a is placed on a first bridge 10, assigned to the first attachment area 6, essentially placed horizontally, attached to the mammal bone 4. Thus, the first attachment area 6 forms the first bridge 10, with a bar shaped design and linking both groups comprising the first set of holes for receiving fastening elements 5a (each with three first holes for receiving fastening elements) to each other. Two bridges 21, with an essentially vertical position relative to the first bridge 10, are then also linked with the first attachment area 6. Each of the bridges 21 is fitted to the first attachment area 6 within the area of a hole for fastening elements 5*a*. The bridges 21 are linking the first attachment area 6 or the first bridge 10 to the second bridge 11, also bar shaped and formed at the second attachment area 7, essentially running parallel to the first bridge 10. Both bridges 21 as well as the second bridge 11 associated with the second attachment area 7, together with the first bridge 10 associated with the first attachment area 6, essentially form a diamond shaped/rectangular frame structure 15*a*.

Similarly, the third attachment area 16 is linked to the second attachment area 7. The third set of holes for fastening elements 5*c* is placed on a third bridge 12, allocated to a third attachment area 16, essentially placed in a horizontal position, attached to the mammal bone 4. Thus, the third attachment area 16 forms the third bridge 12, bar shaped, and linking both groups of the third set of holes for fastening elements 5*c* (each with three holes for receiving fastening elements of the third set 5*c*) to each other. Two bridges 21, with an essentially vertical position relative to the third bridge 12, are then also linked with the third attachment area 16. Each of the bridges 21 is fitted to the third attachment area 16 within the area of a hole for fastening elements 5*c*. The bridges 21 are linking the third attachment area 16 or the third bridge 12 to the fourth bridge 13, also bar shaped and formed at the second attachment area 7, essentially running parallel to the third bridge 12. Both bridges 21 as well as the fourth bridge 13 associated with the second attachment area 7, together with the third bridge 12 associated with the third attachment area 16, essentially form a second diamond shaped/rectangular frame structure 15*b*.

In this design, the first frame structure 15*a* varies slightly from the second frame structure 15*b*. The second frame structure 15*b* is formed differently in so far as the distance between the third and fourth bridge 12, 13 is greater than the distance between the first and second bridge 10, 11.

The third set of holes for fastening elements is formed similarly to the first and second set of holes for fastening elements 5*a*, 5*b*. The holes for receiving fastening elements 5*a*, 5*b*, 5*c* all provide reception for fastening elements in the usual manner, shaped as bone screws, with each of the holes for fastening elements 5*a*, 5*b*, 5*c* displaying a conic screw head fitting area 20 on the side facing away from the bone sections 2, 3, respectively. With the bone joining implant 1 attached to both bone sections 2, 3, the screw heads of the bone screws will then be completely sunk into the holes for fastening elements 5*a*, 5*b*, 5*c*.

As clearly shown by the interaction of FIGS. 1 and 2, the attachment areas 6, 7, 16 as well as a separating tool guidance contour 9, 18 placed on the respective frame structure 15*a*, 15*b* are formed from the same substance or integrally with each other.

In this design, an interior edge, namely, a first interior edge 14*a* of the first bridge 10, directly forms a first separating tool guidance contour 9 prepared to serve as a guiding track for a separating tool, namely, a sawing tool/ buzz saw. The first separating tool guidance contour 9 remodels a first separating line 8 to be created, in the mammal bone 4. Alternatively or additionally, it is possible to design the (second) interior edge 14*b* of the second bridge 11 as a first separating tool guidance contour 9. The first and second interior edges 14*a*, 14*b*, respectively, are the lateral edges of the bridges 10, 11, facing each other.

In addition, the (third) interior edge 14*c* of the third bridge 12 is also designed as a separating tool guidance contour, that is as the second separating tool guidance contour 18.

The second separating tool guidance contour 18 is here also used as a guiding track for a separating tool, namely a sawing tool/buzz saw for separating the first bone section 2 from the second bone section 3. The second separating tool guidance contour 18 remodels a first separating line 17 to be created, in the mammal bone 4. Alternatively or additionally, it is possible to design the (fourth) interior edge 14*d* of the fourth bridge 13 as a second separating tool guidance contour 18. The third and fourth interior edges 14*c*, 14*d*, respectively, are the lateral edges of the bridges 10, 11, facing each other.

The second and fourth bridges 10, 11 are also an integral component of the principal bridge 22 linking both frame structures 15*a*, 15*b* in a dimensionally stable, wing shaped position. It should be pointed out that the principal bridge 22, based on another design, located in a median position between the frame structures 15*a*, 15*b*, is provided with a resealing mechanism, so that the frame structures 15*a*, 15*b* can be attached to bone sections 2, 3 independently from each other and can then again be linked to each other through that mechanism in a dimensionally stable position.

Through its design as an implant, the bone joining implant is formed/made from a biocompatible substance, namely a hardened titanium substance. In addition or alternatively, the bone joining implant 1 can be manufactured, in whole or in part, from a biodegradable substance/be biodegradable.

In connection with FIG. 3 through 9, a procedure for manufacturing the bone implant, based on the invention, is very well displayed. For that purpose, as shown for example in FIG. 3, a 3D model of the existing condition of the mammal bone 4—designed here as a human skull—that is to be treated by osteotomy will be made. This is done by a tomographic imaging procedure (CT procedure), scanning the mammal bone 4 and establishing a first set of data containing/reflecting the three dimensional form of the mammal bone 4.

This mammal bone 4 already shows a malformation of a maxilla/maxilla bone 19 that is to be remedied by dysgnathic, separation surgery/osteotomy treatment. Based on this imaginary 3D model of the existing condition, a 3D target model of the maxilla/the mammal bone 4 will then be created, defining a cutting line 8 or 17, respectively, on the imaginary 3D model of the existing condition for each of the first and third attachment areas 6, 16. The cutting lines 8, 17, placed on the 3D model of the existing condition, are then each assigned one of the separating tool guidance contours 9, 18; that is, they will each be fitted to one of the separating tool guidance contours 9, 18 in accordance with the cutting lines 8, 17. After establishing those two cutting lines 8, 17, an imaginary separation of bone sections 2, 3 will be performed and they will be moved to the desired relative position, in relation to each other, eventually creating an imaginary 3D target model (calculated in a second data set) in FIG. 9, thus adjusting the attachment areas 6, 7, 16 to the shape of the 3D target model. Attachment areas 6, 7, 16 are adjusted and shaped in relation to each other in a way that will adjust the first and third attachment areas 6, 16 for a laminar fitting with the first bone section 2, and of the second attachment area 7 for a laminar fitting with the second bone section 2.

Figure 3:
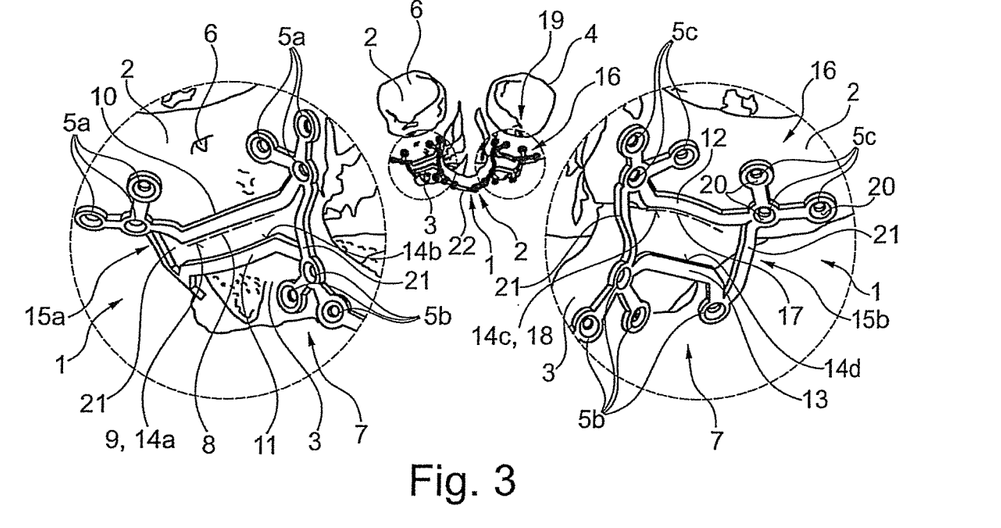
FIG. 3 a frontal view of a 3D model of a mammal bone, formed as a human skull, based on the existing condition, with the first and third attachment areas of the bone joining implant according to FIGS. 1 and 2, respectively, and based on the two subordinate, detailed representations attached to a skull maxilla and the separation lines on the separating tool guidance contour displayed with optic enhancement.
Figure 4:
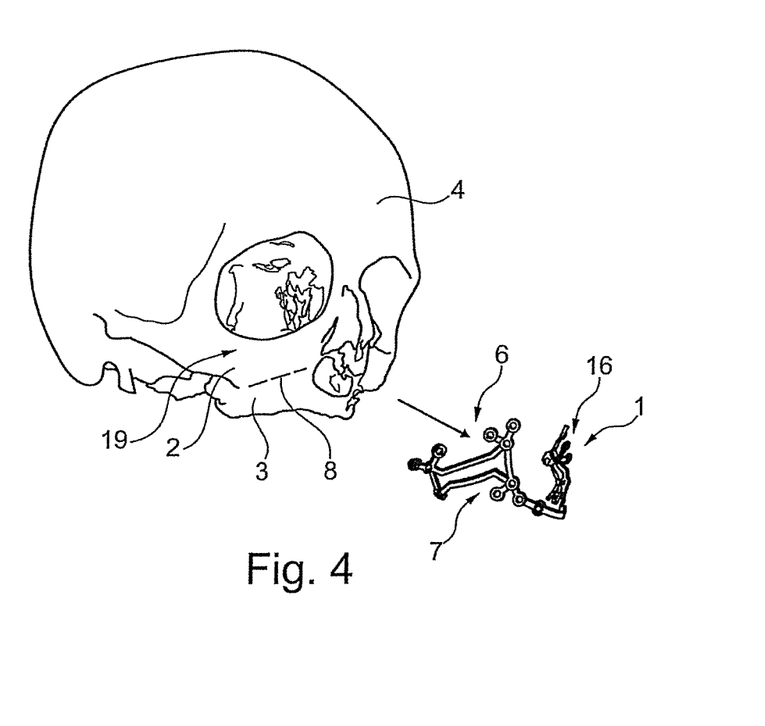
FIG. 4 an isometric representation of the 3D model of the existing condition shown in FIG. 3 after performance of a partial cut in the maxilla along the separating tool guidance contour made by a separating tool, followed by removal of the bone joining implant from the 3D model of the existing condition.
Figure 5:
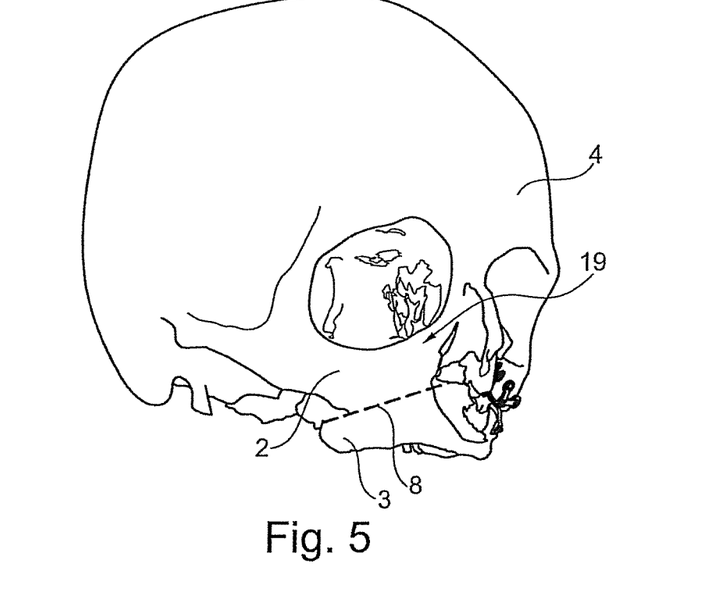
FIG. 5 an isometric representation of the 3D model of the existing condition after performance of a complete cut of the maxilla along the previously partially formed separating lines, with optic enhancement of a separation line.
Figure 6:
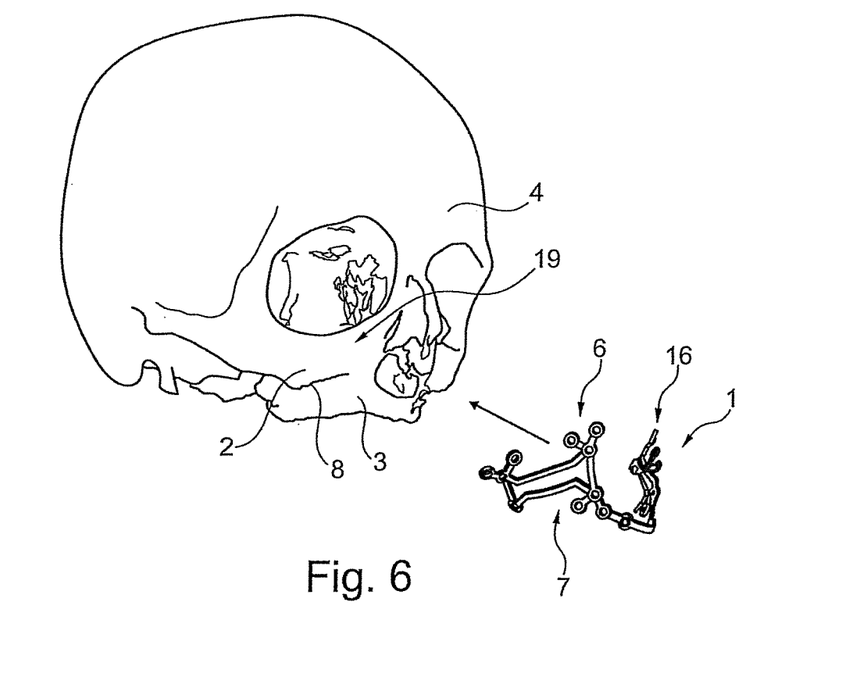
FIG. 6 an isometric representation of the 3D model of the existing condition with both previously separated maxilla bone sections prior to re-attachment of the bone joining implant.
Figure 7:
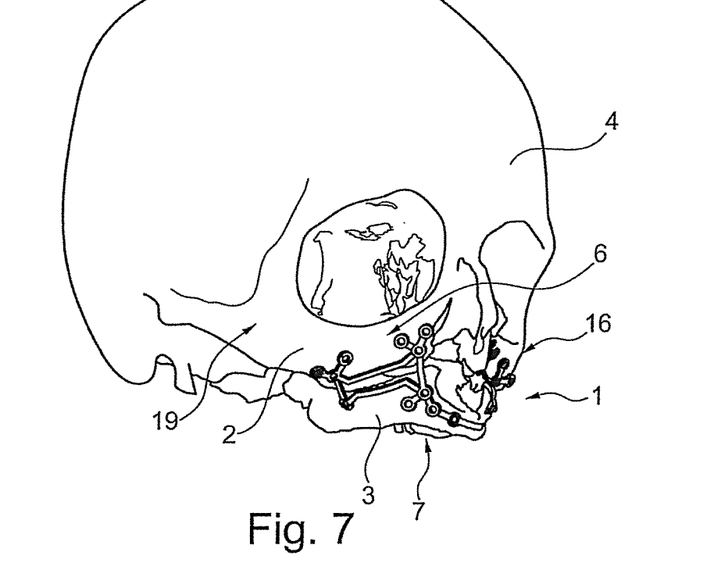
FIG. 7 an isometric representation of the 3D model of the existing condition with the bone joining implant re-attached, where the first and third attachment areas are attached again to the first bone section, while the second attachment area is still distanced from the second bone section.
Figure 8:
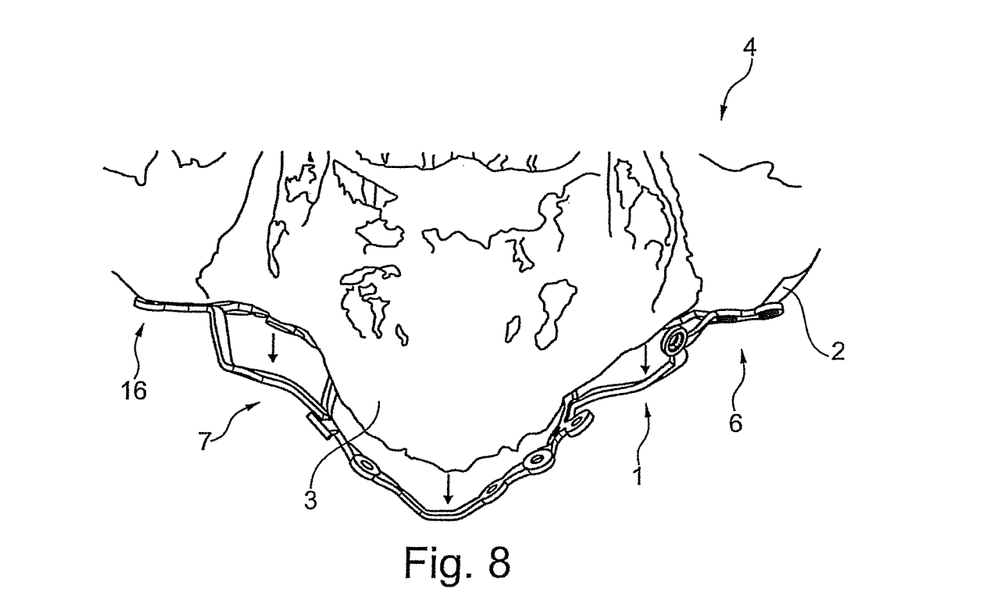
FIG. 8 a view from underneath the 3D model of the existing condition, showing the skull from underneath, with the second bone section being moved along the moving arrows in relation to the first bone section until the second bone section fits with the second attachment area.
Figure 9:
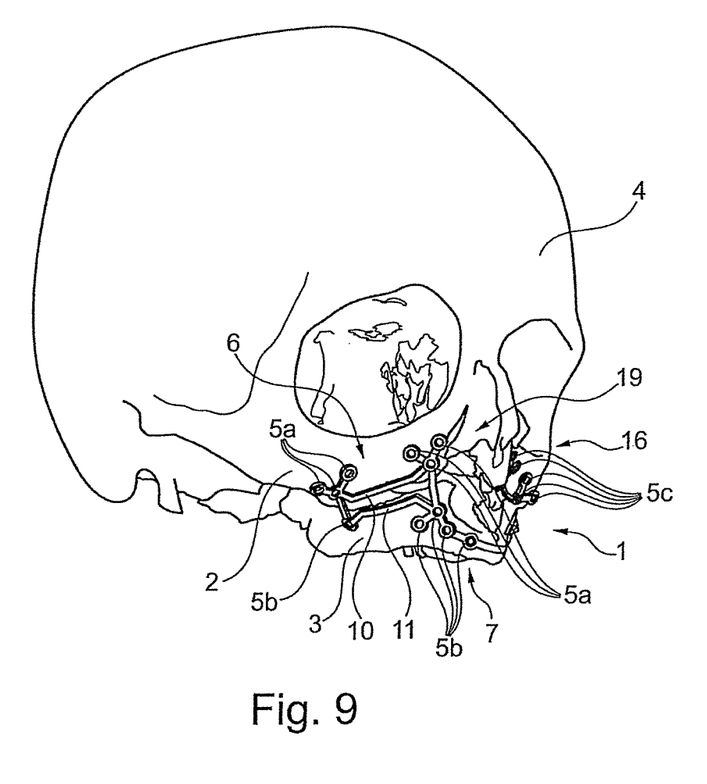
FIG. 9 an isometric representation of the 3D model of the existing condition with a fully attached bone joining implant, firmly attached in both the first and the third, as well as the second attachment areas, to the first and second bone section, respectively, and FIG. 10 an additional design with a wave or zigzag formation of the underside of an upper bridge.

Also, in connection with FIG. 3 through 9, a treatment for the mammal bone 4/skull is very well displayed. For that purpose, the existing bone joining implant 1, using the first and third attachment areas 6, 16, is attached to the mammal bone 4, while the second attachment area 7 is still separated from the second bone section 3 of the maxilla (FIG. 3). Then, along the cutting lines 8, 17, formed by the separating tool guidance contours 9 and 18, the two bone sections 2, 3 will be partially separated within the frame structures 15a and 15b, as shown in the detailed illustrations in FIG. 1. After that, in accordance with FIG. 4, the bone joining implant 1 will be separated and removed from the first bone section 2 and the first bone section 2, in accordance with FIG. 5, will be completely separated from the second bone section 3 by additional sawing along the defined cutting line 8, 17. After complete separation of the bones sections 2 and 3, the bone joining implant 1 will be re-attached with the first and the first attachment area 16 to the first bone section 2 (FIG. 6), inserting a bone screw into each of the holes for fastening elements 5a, 5c, that will also be screwed into the first bone section 2. When both attachment areas 6 and 16 are attached to the first bone section 2 according to FIG. 7, the second bone section 3, separated from the first bone section, is moved according to FIG. 8 in relation to the first bone section 2 until the second bone section fits, according to FIG. 9, with the second attachment area 7, in particular within the area of the second set of holes for fastening elements 5b. In this desired, corrected position between the first and second bone sections 2, 3, several bone screws will then be inserted into the second set of holes for fastening elements 5b, and screwed into the second bone section 3. Ultimately, this resulted in both bone sections 2, 3 being firmly attached to each other by means of the bone joining implant 1.

In other words, the concept of the invention is to join a sawing template with a patient-specific orthognathic implant to create a combination sawing and positioning implant. It is particularly beneficial that any poisoning aids such as splints, navigation devices, marking screws and milling lines can be eliminated. No additional drilling template is required. In addition, precision of the planned implementation and surgical intervention will be enhanced, which in turn alleviates bacterial exposure by eliminating any additional potential germ carriers. The surgical procedure will be facilitated by reducing the individual steps of surgical intervention. Also, the operating time will be reduced by eliminating any additional exchange of instruments and by reduction of the individual steps. This will ultimately provide for a more cost efficient production due to reduction of production steps.

Based on the invention, the design of the bone joining implant 1 comprises two bridges per side, horizontally aligned (10, 11; 12, 13), located in the right and left maxillary sinus wall, respectively, extending from the crista zygomaticoalveolaris to each lateral side of the foramen piriformis. Those two bridges (10, 11; 12, 13), through the in between space/slot thus created, form a guidance that corresponds to a sawing template. The in between space can also run parallel if a bone resection is to be performed. In that case, the lower edge (14a; 14c) of the upper bridge, and the upper edge of the lower bridge (14b; 14d) will serve as a guidance for the osteotomy. If necessary, drilling holes may be placed on the bridges (10, 11; 12, 13) in order to create additional fixation points. The horizontally aligned bridges (10, 11; 12, 13) are attached to four vertically aligned bridges 21, representing a link between the upper and lower pair of bridges (10, 11; 12, 13). The intended shifting information will be encrypted in this area by bending. Both horizontally aligned bridges (10, 11; 12, 13) on the left and right are each linked, in the outer (lateral) area, to a vertical bridge 21, to obtain sufficient stability in this area. If necessary, they can be elongated towards the cheek bone in order to obtain additional fixation points with osteosynthesis screws (bone screws). In a paranasal position on both sides, there are vertically aligned bridges with drilling holes for additional fixation. Below the spina nasales, the right and left sides are linked by a horizontally aligned bridge (10, 11; 12, 13). This link may also be created in situ in the spina nasales area by anchoring or using the lock and key model during surgery so that a large implant can initially be disassembled into smaller individual parts. This type of implant may also be provided for several jaw sections, such as the three part LeFort I osteotomy.

Figure 10:
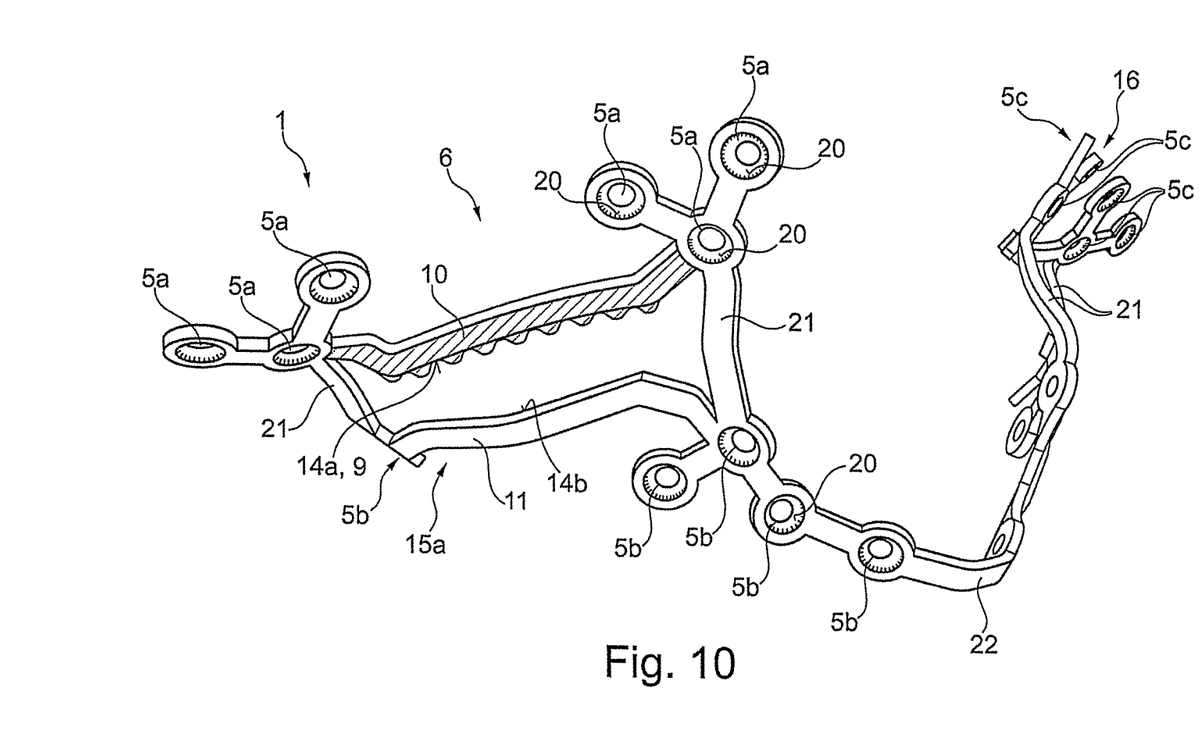

While FIG. 10 is only a representation of the wavy underside of a bridge 10, several such geometrically alternating structures may exist, particularly in those areas used as a separating tool guidance contour 9, the advantage being a reduction of the fitting area for the tool used for bone separation, such as a saw blade. A further thought is that it would make sense to be able to separate the "saw guiding area" after performing the sawing cut, possibly by nipping it off, similarly to a 'Revell building set", in order to reduce material input. Then the form could also be shaped like a guidance slot where, for instance, an oscillating knife could be guided. The "fastening bar" could have a "wavy shape", at least on one side, possibly on two sides in order to minimize the contact area with the saw blade.

LIST OF REFERENCES

1 Bone joining implant
2 First bone section
3 Second bone section
4 Mammal bone
5a First hole for fastening elements
5b Second hole for fastening elements
5c Third hole for fastening elements
6 First attachment area
7 Second attachment area
8 First cutting line
9 First separating tool guidance contour
10 First bridge
11 Second bridge
12 Third bridge
13 Fourth bridge
14a First interior edge
14b Second interior edge
14c Third interior edge
14d Fourth interior edge
15a First frame structure
15b Second frame structure
16 Third attachment area
17 Second cutting line
18 Second separating tool guidance contour
19 Maxilla bone
20 Screw head fitting area
21 Bridging bar
22 Principal bar

I claim:
1. An osteotomy method comprising the steps of:
obtaining a 3D model of the existing configuration of a bone;
determining a cutting line on said 3D model of the existing configuration for separation of one or more bone sections from said bone;
creating a 3D target model from said 3D model of the existing configuration, said 3D target model illustrating the position of said cutting line and a desired repositioning of said one or more bone sections relative to said bone;

manufacturing a bone joining implant based on said 3D target model, said bone joining implant being manufactured to comprise a first attachment area having holes for receiving fastening elements for attachment of said first attachment area to said bone, a second attachment area linked to the first attachment area, said second attachment area having holes for receiving fastening elements for attachment of said second attachment area to said one or more bone sections, and a separating tool guidance contour providing a guide for the cutting of said cutting line between said first and second attachment areas to separate said one or more bone sections from said bone;

wherein said bone joining implant is configured to properly locate said cutting line after attachment of said first attachment area to said bone and prior to attachment of said second attachment area to said one or more bone sections; and further wherein said bone joining implant is configured to properly reposition said one or more bone sections relative to said bone after said one or more bone sections have been separated from said bone and after attachment of said second attachment area to said one or more bone sections;

attaching said first attachment area of said bone joining implant to said bone;

separating said one or more bone sections from said bone along said cutting line utilizing said separating tool guidance contour to guide a separating tool; and attaching said second attachment area of said bone joining implant to said one or more bone sections without detaching said first attachment area.

2. The osteotomy method of claim 1, further comprising the step of determining a second cutting line on said 3D model of the existing configuration for separation of one or more bone sections from said bone;

wherein said step of creating said 3D model further comprises illustrating the position of said second cutting line;

wherein said step of manufacturing said bone joining implant further comprises said bone joining implant being manufactured to comprise a third attachment area having holes for receiving fastening elements for attachment of said third attachment area to said bone and a second separating tool guidance contour providing a guide for the cutting of said second cutting line between said first and third attachment areas to separate said one or more bone sections from said bone;

wherein said bone joining implant is configured to properly locate said second cutting line after attachment of said first attachment area to said bone section and prior to attachment of said third attachment area to said one or more bone sections; and further wherein said bone joining implant is configured to properly reposition said one or more bone sections relative to said bone after said one or more bone sections have been separated from said bone and after attachment of said third attachment area to said one or more bone sections;

separating said one or more bone sections from said bone along said second cutting line utilizing said second separating tool guidance contour to guide said separating tool; and attaching said third attachment area of said bone joining implant to said one or more bone sections without detaching said first attachment area.

3. The method of claim 1, wherein said step of manufacturing said 3D target model further comprises said bone joining implant being manufactured such that said first attachment area has a contour matching the contour of the bone at the desired attachment location of said first attachment area and said second attachment area has a contour matching the contour of said one or more bone sections at the desired attachment location of said second attachment area upon repositioning of said one or more bone sections.

4. The method of claim 2, wherein said step of manufacturing said 3D target model further comprises said bone joining implant being manufactured such that said first attachment area has a contour matching the contour of the bone at the desired attachment location of said first attachment area, said second attachment area has a contour matching the contour of said one or more bone sections at the desired attachment location of said second attachment area upon repositioning of said one or more bone sections, and said third attachment area has a contour matching the contour of said one or more bone sections at the desired attachment location of said third attachment area upon repositioning of said one or more bone sections.

5. The osteotomy method of claim 1, wherein said separating tool guidance contour is manufactured to comprise a frame structure formed between said first and second attachment areas.

6. The osteotomy method of claim 5, wherein said second separating tool guidance contour is manufactured to comprise a frame structure formed between said first and third attachment areas.

7. The osteotomy method of claim 1 wherein said separating tool guidance contour comprises a bridging bar linked with said first attachment area and/or said second attachment area.

8. The osteotomy method implant of claim 2 wherein said separating tool guidance contour comprises a bridging bar linked with said first attachment area and/or said third attachment area.

9. The osteotomy method of claim 1, wherein said step of obtaining a 3D model of the existing configuration of a bone is performed by tomographic imaging.

10. The osteotomy method of claim 2, wherein said step of obtaining a 3D model of the existing configuration of a bone is performed by tomographic imaging.

11. An osteotomy method for separating, repositioning and reattaching bone sections from a bone such that the bone is reconfigured, the method comprising the steps of:

obtaining a 3D model of the existing configuration of a bone using tomographic imaging;

determining the location of a cutting line on said 3D model of the existing configuration of said bone for separation of one or more bone sections from said bone;

creating a 3D target model from said 3D model of the existing configuration of said bone, said 3D target model illustrating the position of said cutting line and a desired repositioning of said one or more bone sections relative to said bone upon reattachment of said one or more bone segments;

utilizing said 3D target model to manufacture a bone joining implant, said bone joining implant being manufactured to comprise a first attachment area having holes for receiving fastening elements for attachment of said first attachment area to said bone, a second attachment area linked to the first attachment area, said second attachment area having holes for receiving fastening elements for attachment of said second attachment area to said one or more bone sections, and a separating tool guidance contour providing a guide for the cutting of said cutting line between said first and second attachment areas to separate said one or more bone sections from said bone;

wherein said bone joining implant is configured to properly locate said cutting line after attachment of said first attachment area to said bone and prior to attachment of said second attachment area to said one or more bone sections; and further wherein said bone joining implant is configured to properly reposition said one or more bone sections relative to said bone after said one or more bone sections have been separated from said bone and after attachment of said second attachment area to said one or more bone sections;

attaching said first attachment area of said bone joining implant to said bone;

separating said one or more bone sections from said bone along said cutting line utilizing said separating tool guidance contour to guide a separating tool; and attaching said second attachment area of said bone joining implant to said one or more bone sections without detaching said first attachment area.

12. The osteotomy method of claim 11, further comprising the step of determining a second cutting line on said 3D model of the existing configuration for separation of one or more bone sections from said bone;

wherein said step of creating said 3D model further comprises illustrating the position of said second cutting line;

wherein said step of utilizing said 3D target model to manufacture said bone joining implant further comprises said bone joining implant being manufactured to comprise a third attachment area having holes for receiving fastening elements for attachment of said third attachment area to said bone and a second separating tool guidance contour providing a guide for the cutting of said second cutting line between said first and third attachment areas to separate said one or more bone sections from said bone;

wherein said bone joining implant is configured to properly locate said second cutting line after attachment of said first attachment area to said bone section and prior to attachment of said third attachment area to said one or more bone sections; and further wherein said bone joining implant is configured to properly reposition said one or more bone sections relative to said bone after said one or more bone sections have been separated from said bone and after attachment of said third attachment area to said one or more bone sections;

separating said one or more bone sections from said bone along said second cutting line utilizing said second separating tool guidance contour to guide said separating tool; and attaching said third attachment area of said bone joining implant to said one or more bone sections without detaching said first attachment area.

13. The method of claim 11, wherein said step of utilizing said 3D target model to manufacture said bone joining implant further comprises said bone joining implant being manufactured such that said first attachment area has a contour matching the contour of the bone at the desired attachment location of said first attachment area and said second attachment area has a contour matching the contour of said one or more bone sections at the desired attachment location of said second attachment area upon repositioning of said one or more bone sections.

14. The method of claim 12, wherein said step of utilizing said 3D target model to manufacture said bone joining implant further comprises said bone joining implant being manufactured such that said first attachment area has a contour matching the contour of the bone at the desired attachment location of said first attachment area, said second attachment area has a contour matching the contour of said one or more bone sections at the desired attachment location of said second attachment area upon repositioning of said one or more bone sections, and said third attachment area has a contour matching the contour of said one or more bone sections at the desired attachment location of said third attachment area upon repositioning of said one or more bone sections.

15. The osteotomy method of claim 11, wherein said separating tool guidance contour is manufactured to comprise a frame structure formed between said first and second attachment areas.

16. The osteotomy method of claim 15, wherein said second separating tool guidance contour is manufactured to comprise a frame structure formed between said first and third attachment areas.

17. The osteotomy method of claim 11 wherein said separating tool guidance contour comprises a bridging bar linked with said first attachment area and/or said second attachment area.

18. The osteotomy method implant of claim 12 wherein said separating tool guidance contour comprises a bridging bar linked with said first attachment area and/or said third attachment area.

* * * * *